United States Patent
Singh

(10) Patent No.: US 6,190,913 B1
(45) Date of Patent: Feb. 20, 2001

(54) METHOD FOR CULTURING CELLS USING WAVE-INDUCED AGITATION

(75) Inventor: Vijay Singh, 391 Mount Harmony Rd., Bernardsville, NJ (US) 07924

(73) Assignee: Vijay Singh, Bernardsville, NJ (US)

( * ) Notice: Under 35 U.S.C. 154(b), the term of this patent shall be extended for 0 days.

(21) Appl. No.: 09/138,590

(22) Filed: Aug. 22, 1998

Related U.S. Application Data

(60) Provisional application No. 60/055,592, filed on Aug. 12, 1997.

(51) Int. Cl.[7] ............................... C12N 5/02; C12N 5/06; C12N 5/08
(52) U.S. Cl. ............................... 435/394; 435/383
(58) Field of Search ..................... 435/383, 394

(56) References Cited

U.S. PATENT DOCUMENTS

| | | | |
|---|---|---|---|
| 3,102,082 | * | 8/1963 | Brewer ................................ 435/30 |
| 4,140,162 | * | 2/1979 | Gajewski et al. ................. 435/297.5 |
| 4,847,462 | * | 7/1989 | Soodak et al. ................... 219/121.63 |
| 5,071,760 | * | 12/1991 | Watanabe et al. ............... 435/240.25 |
| 5,686,304 | * | 11/1997 | Codner .................................. 435/325 |
| 5,843,673 | * | 12/1998 | Sharpe-Timms ...................... 435/7.1 |
| 5,932,467 | * | 8/1999 | Khan et al. ......................... 435/235.1 |

FOREIGN PATENT DOCUMENTS

280054 * 8/1988 (EP) .

* cited by examiner

Primary Examiner—Jon P. Weber

(57) ABSTRACT

The present invention provides a novel apparatus for culturing animal, insect, microbial, or plant cells whereby an inflated plastic bag provides a sterile, disposable cultivation chamber. The inflated bag is partially filled with liquid cultivation media and cells, and placed on rocking mechanism that moves the bag to and fro thereby inducing a wave-like motion to the liquid contained therein. This motion ensures cell suspension, bulk mixing, and oxygen transfer from the liquid surface to the respiring cells without damaging shear forces or foam generation. Air is passed through the bag to provide oxygen, and sweep out evolved carbon dioxide.

9 Claims, 4 Drawing Sheets

Side view of the apparatus showing bag filled with media and rocking mechanism.

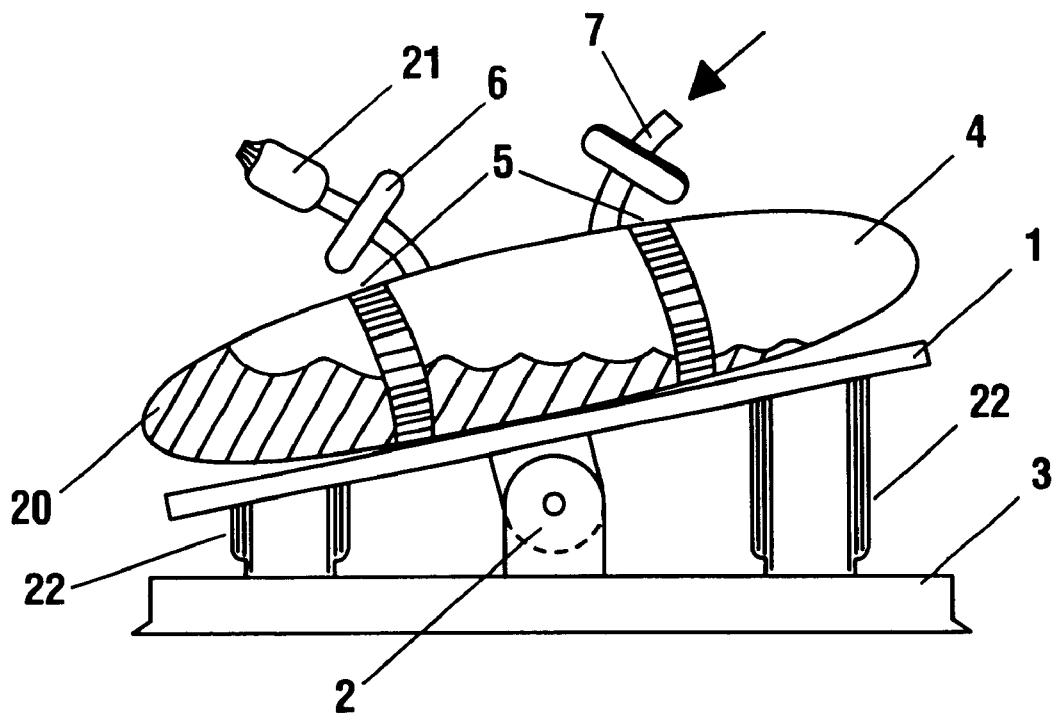
FIG 1. Side view of the apparatus showing bag filled with media and rocking mechanism.

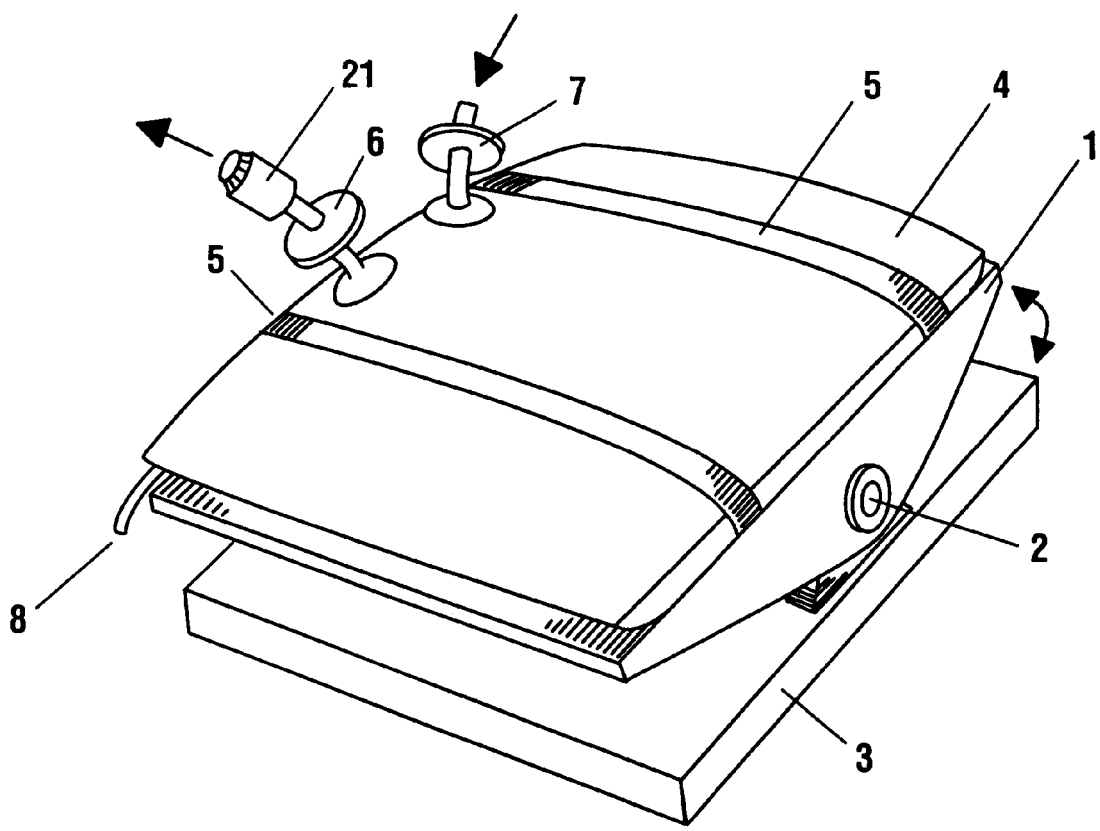
FIG 2. Perspective View of the Apparatus

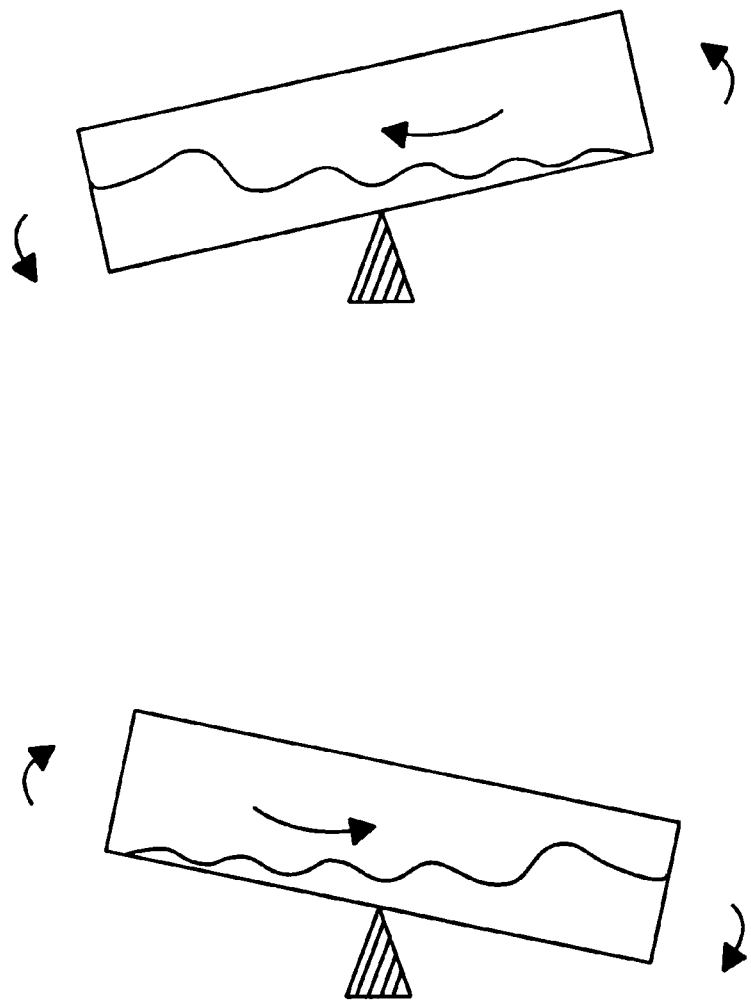
FIG 3. Formation of Waves as a Result of Rocking Motion

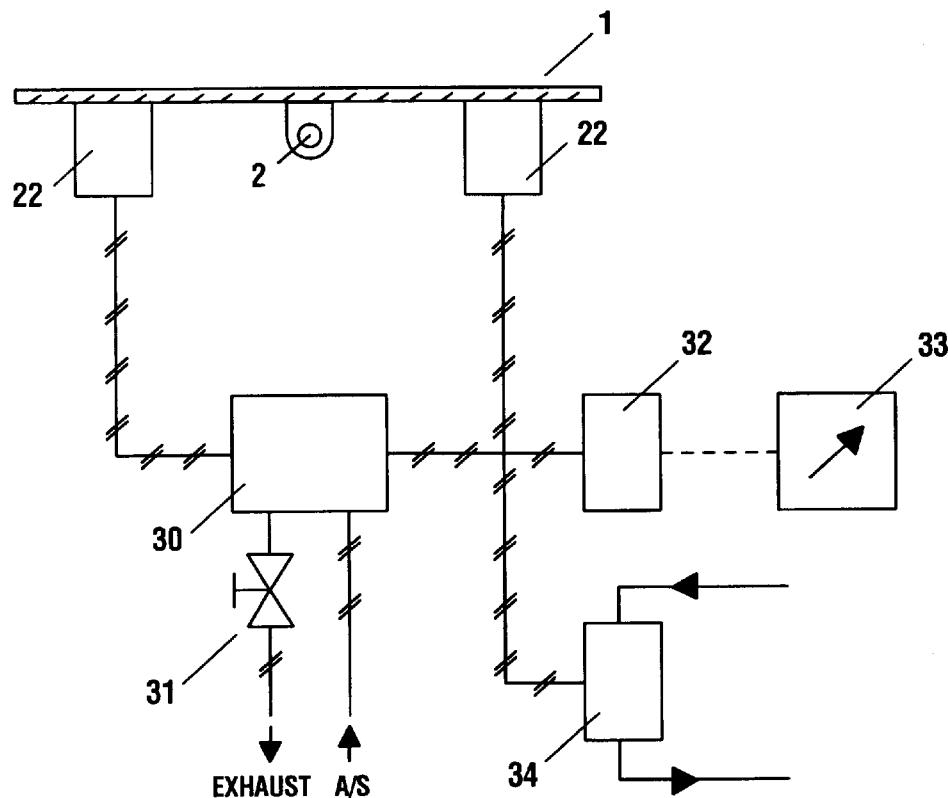
FIG 4. Schematic of pneumatic and electronic circuits

METHOD FOR CULTURING CELLS USING WAVE-INDUCED AGITATION

This application claim priority to U.S. Provisonal 60/055,592 filed Aug. 12, 1997.

REFERENCES CITED

U.S. PATENT DOCUMENTS

| | |
|---|---|
| 4,661,455 | Hubbard |
| 4,906,577 | Armstrong et al |
| 5,002,890 | Morrison |
| 5,443,985 | Lu |
| 5,057,429 | Watanabe et al |
| 5,225,346 | Matsumiya et al |
| 5,202,254 | Amoit et al |
| 5,135,853 | Dziewulski et al |

BACKGROUND

1. Field of the Invention

The present invention relates to a cell culture apparatus useful for the cultivation of animal, insect, micobial, or plant cells in industrial or medical applications.

2. Background—Description of Prior Art

In vitro cell culture is an important operation for the production of pharmaceuticals such as antibodies, cytokines, viral gene vectors, and for cell therapy. Many devices have been developed for cell culture. These can be divided into two major categories: 1) small-scale devices with a culture volume of 1 to 2 liters; and 2) bioreactors with operating volumes of 1 to 10,000 liters. The small-scale devices are limited to a few liters in volume because these devices rely on surface oxygen transfer to provide the required aeration for cells to grow and make the desired product. Such devices include spinner flasks, T-flasks, roller bottles, and gas-permeable bags. Their limitation on culture volume is very serious because many applications require 10 to 100 liters of cell culture in order to produce sufficient quantity of the product of interest. Using conventional small-scale equipment, this requires the tedious production of multiple batches.

Traditionally, production of larger volumes has required the use of bioreactors. Bioreactors, however, require elaborate mechanical systems to provide aeration and mixing. Control systems are required to sterilize the equipment and regulate temperature, pH and dissolved oxygen levels. This makes a bioreactor expensive to acquire, install, maintain and operate. Extensive training is required to operate these bioreactors without contamination. For these reasons bioreactors are only used in large industrial and academic environments. The conventional cell culture bioreactor is a stirred tank that has been adapted from microbial cultivation by the addition of low-shear mixers and more gentle aeration systems. (Armstrong et al U.S. Pat. No. 4,906,577) and Morrison U.S. Pat. No. 5,002,890.

These improvements are relatively minor and very little real innovation has been made since the 1960's.

In examining the many cell cultivation device patents it is apparent that most have been commercial failures due to: 1) failure to provide an appropriate environment for cell cultivation, and 2) excessive complexity. The patent by Lu et al (U.S. Pat. No. 5,443,985) is an example of the first problem. Here, the inventors after discussing the detrimental effects of bubbles in cell culture propose a cultivation device in which both agitation and aeration is accomplished solely by bubbling air into the device. An example of excessive complexity with little benefit is U.S. Pat. No. 5,057,429 (Watanabe et al). Here a gas permeable bag is used to diffuse oxygen and nutrients to the cells. A second inner bag contains the cells. An elaborate agitation apparatus with complex motion is described. However, the device is essentially oxygen transfer limited by the surface to volume ratio of the gas permeable surface. It is thus not possible to scale the unit beyond a few liters. A more or less similar result is achieved using the static gas-permeable bag described by Matsumiya et al (U.S. Pat. No. 5,225,346). Of course, as with all devices that rely on gas-permeable surfaces, scale-up is severely restricted. Amoit et al (U.S. Pat. No. 5,202,254) describe improvements to the hollow fiber bioreactor. However, their ideas do not address the fundamental problems of the hollow fiber devices. These are formation of oxygen and nutrient gradients in the system; lack of mixing; difficulty in sampling and the complexity of the support system (oxygenator, pump, instrumentation and circulation tubing). A recent patent by Dziewulski et al (U.S. Pat. No. 5,135,853) continues the trend in the field to ever more complex cultivation devices by introducing a three-compartment bioreactor.

Instead, it is necessary to reduce the complexity of the cultivation apparatus by understanding and exploiting the unique characteristics of cell cultivation. For design to be successful it must therefore:

Eliminate gas bubbles which are now known to cause cell damage.

Eliminate high local shear caused by rotating mixers.

Provide sufficient mixing to provide a homogeneous environment, prevent cell settling, and promote as transfer.

Provide a sterile, disposable cultivation vessel to reduce labor cost and the need for steam sterilization.

Not use permeable membranes or static surface aeration in order to facilitate scale-up.

Reduce mechanical and instrumentation complexity to a minimum.

The present invention will provide a new and improved method for culturing cells in vitro that achieves all these criteria, and overcomes all the aforementioned prior art limitations.

Objects and Advantages

Key objects and advantages of the present invention are:

(a) Reduces the cost of a cell culture bioreactor by a factor of 100 compared to conventional glass and stainless steel stirred tank bioreactors.

(b) Provides a non-invasive means of agitation that reduces mechanical complexity and possibility of contamination. This mode of agitation minimizes local high shear fields that cause cell damage.

(c) Improves cell growth and productivity by providing a bubble-free means of aeration that minimizes damage to cells caused by bubbles and foam formation.

(d) Provides an easy to operate culture device suitable for industrial and hospital environments. It eliminates the need for labor-intensive cleaning, preparation and sterilization, typical of conventional stainless steel bioreactor equipment by providing a pre-sterilized disposable one-use device. The low mechanical complexity of the present invention reduces operating and maintenance costs.

(e) Provides complete isolation of cells allowing cultivation in a non-aseptic environment, and is also useful for the culture of pathogens, viruses and other organisms requiring a high degree of containment.

(f) Can be operated with widely varying culture volume. This allows for seed buildup within the culture vessel by adding media without the need for seed bioreactors and contamination-prone vessel-to-vessel transfers.

Further objects and advantages of my invention of my invention will become apparent from a consideration of the drawings and ensuing description.

BRIEF DESCRIPTION OF THE DRAWINGS

FIG 1 is a side view of the apparatus according to the present invention showing the bag the rocking mechanism.

FIG. 2 is a perspective view of the apparatus.

FIG. 3 shows the formation of waves as a result of the rocking motion.

FIG. 4 is a schematic of the pneumatic and electronic circuits necessary for the operation and control of the bioreactor.

Reference Numerals in Drawings
1 Rocking platform
2 Pivot point for rocking motion
3 Baseplate
4 Bag forming disposable chamber
5 Restraining straps
6 Exhaust gas vent filter
7 Inlet air filter
8 Sampling port
20 Liquid media in bag
21 Pressure control valve
22 Pneumatic pistons
30 Pneumatic control unit
31 Speed control valve
32 Pressure switch
33 Tachometer
34 Pneumatically driven air pump

SUMMARY OF THE INVENTION

The present invention has been developed through many investigations to result in a low cost simple solution to the problem of medium-scale (100 ml to 500 liter) cell culture.

The device consists of a pre-sterilized flexible plastic bag in which cells are cultivated. The bag is partially filled with growth media and the remainder of the bag is continuously purged with air or other oxygen-rich gas. The bag is placed on a platform that can be rocked to and fro. The rocking motion promotes wave formation in the bag which provides liquid mixing and enhances oxygen transfer from the headspace gas to the liquid phase where it is essential for cell growth and metabolism. The air in the bag performs several functions: 1 ) allows the formation of surface waves promoting oxygen transfer; 2) continually provides fresh oxygen into the bag and sweeps out gaseous metabolic products and 3) inflates the bag to a rigid form which reduces foam formation and promotes liquid mixing.

By using a disposable bag as the only contact surface for the cells, the device provides excellent containment and eliminates labor intensive cleaning and sterilization. Lack of any mechanical parts except for the rocking platform dramatically reduces cost and maintenance. The gentle wave agitation provides an intrinsically low shear environment. Aeration is also performed without generating cell-damaging bubbles.

The invention is useful for animal, plant, microbial, and insect cell culture, both in free suspension as well as for anchorage-dependent systems. It is very suitable for virus and pathogen cultivation because of the high degree of containment.

DETAILED DESCRIPTION OF THE PREFERRED EMBODIMENT

A typical embodiment of the invention is shown in FIG. 1 (side view) and FIG. 2 (perspective view). The bioreactor consists of a disposable pre-sterilized plastic bag 4 that rests on rocking platform 1. The platform can rock in one axis about pivot point 2. In the preferred embodiment the platform is made of stainless steel and the pivot point is a nylon bushing through which a stainless steel shaft is passed. However, the rocking platform may consist of any other rigid material such as, plastic, fiberglass, aluminum, etc. Likewise, the pivot point may be a hinge, pin, or other similar device.

The rocking platform 1 may be moved through an angle of 1° to 15° by the alternate actuation of pneumatic pistons 22. Other actuation means such as hydraulic, electric may be employed. Restraining straps 5 prevent the bag from slipping of the platform and also prevent the bag from overinflating. Other means to secure the bag such as a rigid holder, tape, or sleeve may also be used. It is critical that the bag be prevent from overinflation otherwise the bottom surface will not conform to the flat profile of the platform and poor wave action will result. FIG. 3 shows, diagramatically, the liquid wave that forms when the bags rocks from one side to the other. For proper wave motion, it is critical that the bag not be completely full of liquid. In the present embodiment the liquid phase may comprise 10 to 80% of the total bag volume.

The remaining volume of the bag is filled with air or other oxygen containing gas. This gas is introduced through inlet filter 7 which ensures that the air introduced into the bag is sterile. Air is used to initially inflate the bag and also during cultivation. The air flow during cultivation provides oxygen to the cell culture, carbon dioxide to maintain pH, and sweeps out gaseous products of metabolism. Exhaust gases are vented through vent filter 6 which ensures that any organisms in the bioreactor are not discharged to the environment. This ensures containment of the culture. Pressure control valve 21 is designed such that it only opens when pressure in the bag exceeds a predetermined value. This ensures that the bag is always inflated to a predetermined pressure regardless of the airflow rate into the bag. In the preferred embodiment this pressure was set at 1 to 2 inches of water column.

The entire apparatus is placed inside a temperature controlled chamber. Alternatively, the platform may contain an integral heater controlled by a temperature sensor and controller that can be used to maintain a predetermined temperature in the cultivation chamber. The rocking action ensures that a uniform temperature is achieved in the culture fluid. Humidity of the inlet gas may be controlled to reduce evaporation. Other gases, such as carbon dioxide, may be introduced into the chamber to control pH and other environmental conditions.

Cultivation is done by inflating the bag with air, then introducing liquid media into the bag either through a sterile connection such as a Clave® or a sterile tube fuser. The culture is then introduced into the bag using a similar method. Rocking rate and aeration are then set at predetermined values. Samples may be withdrawn by connecting a syringe to sampling port 8. Virus inoculum or media additions can also be added through this port at appropriate times during the cultivation. Harvesting is done by removing the bag from the rocking platform and pumping out the cell culture broth. The next batch can be initiated immediately by placing a new bag on the platform.

In the preferred embodiment bags containing 100 ml to 500 liters of liquid were tested and found to provide sufficient oxygen transfer and mixing for typical cell cultures. Rocking rates are adjustable from 1 to 30 rocks per minute and aeration is adjustable from 0.01 to 0.25 vvm (volume of air per volume of liquid per minute). Adjustment of rocking rate is critical as too high rocking rates will cause excessive foaming and too low a rocking rate will not provide sufficient oxygen transfer. Proper rocking rate is set by increasing the rate until foaming is observed. The rocking rate is then reduced slightly below this rate. Alternatively, the dissolved oxygen levels may be monitored by sampling or using on-line probes and the rocking rate adjusted to maintain the desired dissolved oxygen concentration.

In the preferred embodiment, the entire device is operated pneumatically. In FIG. 4 control unit 30 monitors the pressure in each pneumatic piston 22. When the pressure in a piston is zero the control unit switches to inflate it. This causes the platform 1 to rock to the other side forcing the air out of the opposite piston eventually reducing the pressure in this piston to zero causing the controller to repeat the cycle in the reverse direction. Air control valve 31 regulates the airflow from the exhausting piston, thereby controlling the rocking rate. Pressure switch 32 monitors the pressure pulse caused by each rock and tachometer 33 displays the pulses in units of rocks per minute. Pneumatically driven pump 34 pumps air into the bag to maintain inflation and for oxygen supply as discussed earlier.

The following will refer to examples of cultivating cells using the device of the invention.

EXAMPLE 1

Oxygen Transfer Performance

Cells require oxygen to grow and carry out metabolic activities. Prior art is exemplified by spinner flasks where oxygen transfer and mixing are provided by agitation using a paddle. The oxygen transfer is limited by the gas-liquid surface to liquid volume ratio. As the volume of spinner flasks increases this surface-to-volume ratio decreases, thereby reducing the available oxygen transfer and the maximal cell density that can be achieved. Table 1 compares the performance of spinner flasks and the invention. In this table oxygen transfer is quantitated by the number of moles of oxygen transferred per liter of liquid per hour (volumetric oxygen transfer coefficient $k_L a$). It can be seen from Table 1 that cultivation in spinner flasks is not possible beyond a 1 liter volume due to oxygen limitations. A $k_L a$ of at least 1 ($hr^{-1}$) is required to reach practically useful cell densities (>$1 \times 10^6$ cells/ml). However, the current invention is not limited by oxygen transfer on scale-up and culture volumes of 500 liters have been demonstrated.

TABLE 1

Oxygen Transfer Comparison Prior Art vs Invention ($k_L a$ in 1/hr)

| Volume of liquid in system | $k_L a$ in spinner (prior art) | $k_L a$ in current invention |
|---|---|---|
| 100 ml | 1.94 | 1.61 |
| 1 liter | 0.95 | 1.15 |
| 10 liter | 0.40 (calculated) | 3–4 |
| 100 liter | 0.20 (calculated) | 2–3 |

EXAMPLE 2

Hybridoma Culture Expressing Monoclonal Antibody

The ability of the invention to grow hybridoma cells to final cell densities of up to $5 \times 10^6$ cells/ml was demonstrated. This is comparable, or better than reported prior art. Product expression of the monoclonal antibody was better than achieved in prior art devices. Product expression using a recombinant NS0 cell line expressing a humanized monoclonal antibody was 600 to 700 mg/liter using the current invention. Typical results in small-scale prior art (spinner flasks) was 300 to 500 mg/liter. Expression in larger scale prior art (bioreactors) was 400 to 600 mg/liter (10 liter bioreactor) and 500 to 600 mg/liter (160 liter bioreactors). The invention has the significant advantage that up to 500 liters of cell broth can be cultivated in a single batch. Spinner culture is not possible beyond 1 liter resulting in the tedious need to produce multiple batches in order to produce sufficient quantities of product. The disposable nature of the invention also reduces labor for cleaning and sterilization.

EXAMPLE 3

Recombinant Adenovirus Production in 293 Cells

The ability of the invention for the cultivation of viruses has been demonstrated by the production of recombinant adenovirus in human embryonic kidney 293 cells. In this application the 293 cells were cultivated in the bag bioreactor to a cell density of $2 \times 10^6$ cells/ml. The contents were then diluted 1:1 with fresh media and adenovirus inoculum added. Harvest was performed after two days when compete cell lysis was observed. Virus titer was 20,000 plaque forming units per cell which was comparable to that obtained in a variety of other bioreactors. The current invention, has the considerable advantage of large operating volume, very gentle agitation and complete containment of the virus from the environment.

EXAMPLE 4

Insect Cell (sF9) Culture

Insect cells are used for the production of recombinant proteins because of their high expression and case of genetic engineering. However, the oxygen requirements of insect cells are higher than that of animal cells. This necessitates the use of complex bioreactors for culture volumes larger than 500 ml. The current invention provides much higher oxygen transfer than prior art (spinners) and maintains this higher oxygen transfer from systems of 100 ml culture to 500 liters. This enables the culture of insect cells in this simple system. Maximal cell density achieved was over $5 \times 10^6$ cells/ml which was comparable or higher than reported for prior art systems. Baculovirus titer on infection of these cells and eventual product expression was also comparable or better than reported for prior art demonstrating that oxygen transfer is not limiting in the current invention.

EXAMPLE 5

Anchorage Dependent Cell Culture

The examples thus far have used cell culture in free suspension. Many cell lines do not grow well in suspension but instead need a support surface to which they attach. It is possible to grow such anchorage-dependent systems in the current invention. In this example 5 g/liter of microcarrier beads (Cytodex 3 beads manufactured by Pharmacea, Inc) were introduced into a bag containing grow media. Human embryonic kidney 293 cells were detached from a seed T-flask and the cell suspension was introduced into the bag. Cells were allowed to contact the microcarrier surface for several hours to ensure attachment. Agitation was then started by rocking at a slow rate of 5 to 10 rocks per minute. Cells continued to remained attached to the microcarrier surface and covered the entire available surface (100% confluent) in 48 hours. These growth kinetics were very similar to microcarrier culture of this cell line in small conventional spinner flasks.

While this example demonstrates the use of microcarriers in the bag for anchorage dependent cell culture it is obvious that other anchorage substrates such as fibers, sheets, beads etc. could be employed in the invention.

As mentioned above, according to the present invention, the following advantages could be brought about.

(1) Provide an excellent environment for cell growth and expression due to the low shear generated by the gentle wave agitation and bubble-free aeration system. Prior art utilized mechanical mixers that impart high local shear, high-shear pumparound devices, or static culture that is incapable of scale-up.

(2) In comparison to prior art, this invention allows the cultivation of much larger volumes of broth in a single batch.

(3) The cultivation is possible without the external circulation of media liquid as is done in hollow fiber devices. External circulation greatly increases the risk of contamination.

(4) The cultivation is possible without the need for in-situ sterilization as is required in conventional bioreactors. This reduces cost and complexity. The disposable presterilized bag guarantees sterile operation.

(5) The cultivation is possible without pumps or instrumentation for control of pH or dissolved oxygen. Temperature control can be achieved by simply placing the invention inside a common laboratory incubator.

(6) Cultivation is possible without the need for an expensive sterile environment such as a laminar flow cabinet.

(7) Cultivation is possible without extensive or specialized training.

Accordingly, there has been illustrated add described herein a preferred form of the present invention. It is envisioned that those skilled in the art nay devise various alternative designs or modifications, once possessed with a disclosure of the present invention. Insofar as such alternative designs or modifications are encompassed by the claims appended hereto, they are deemed to fall within the spirit and scope of the present invention as defined by said claims.

What is claimed is:

1. A method for the cultivation of cells comprising the steps of:

providing a pre-sterilized plastic bag having a volume of at least five liters, the bag having a single hollow interior chamber;

partially filling the bag with a gas containing oxygen to thereby partially inflate the bag;

introducing a liquid media and a cell culture into the bag, wherein the liquid media and the cell culture comprise between 10 to 80% of the volume of the bag;

filling the remainder of the bag with the gas such that the bag becomes rigid;

securing the bag to a platform;

rocking the platform in a single degree of freedom to thereby induce a wave motion to the liquid media in the bag, whereby the necessary oxygen transfer and mixing required for cell growth and productivity is accomplished by the wave motion.

2. The method of claim 1, wherein the rocking step further comprises rocking the platform in a single degree of freedom through a predetermined angle.

3. The method of claim 2, wherein the predetermined angle is in the range of 1 to 15 degrees from a horizontal position of the platform.

4. The method of claim 1, wherein the rocking step further comprises rocking the platform at a predetermined rate.

5. The method of claim 3, wherein the predetermined rate is in the range of 1 to 30 rock per minute.

6. The method of claim 1, further comprising the steps of:

introducing the gas containing oxygen into the bag during the rocking step; and exhausting products of respiration from the bag during the rocking step.

7. The method of claim 6, wherein the steps of introducing the gas and exhausting the products of respiration during the rocking step further comprise introducing the gas and exhausting the products of respiration at a controlled rate.

8. The method of claim 1, wherein said cells are of animal, human, insect, microbial, or plant origin.

9. The method of claim 1, wherein said cells are used for the production of virus.

* * * * *